US00PP22448P3

(12) United States Plant Patent
Bacon

(10) Patent No.: US PP22,448 P3
(45) Date of Patent: Jan. 10, 2012

(54) NECTARINE TREE NAMED 'SUNECTWENTYTWO'

(50) Latin Name: ***Prunus persica* var. *nucipersia***
Varietal Denomination: Sunectwentytwo

(75) Inventor: Terry Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 124 days.

(21) Appl. No.: 12/657,348

(22) Filed: Jan. 19, 2010

(65) Prior Publication Data

US 2011/0179536 P1 Jul. 21, 2011

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

| | | | | |
|---|---|---|---|---|
| PP7,305 | P | 8/1990 | Zaiger et al. | |
| PP13,501 | P2 | 1/2003 | Zaiger et al. | |
| PP19,363 | P3 * | 10/2008 | Zaiger et al. | Plt./190 |
| PP19,588 | P3 * | 12/2008 | Zaiger et al. | Plt./190 |
| PP20,314 | P2 * | 9/2009 | Chaparro | Plt./190 |

* cited by examiner

*Primary Examiner* — Wendy C Haas
(74) *Attorney, Agent, or Firm* — Knobbe, Martens, Olson & Bear, LLP

(57) ABSTRACT

A new and distinct nectarine tree variety, *Prunus persica* var. *nucipersica,* cv. 'Sunectwentytwo' is characterized by early harvest and large sized fruit.

1 Drawing Sheet

Latin name of the genus and species claimed: *Prunus persica* var. *nucipersica.*

Variety denomination: 'Sunectwentytwo'.

BACKGROUND AND SUMMARY OF THE INVENTION

This invention relates to the discovery and asexual propagation of a new and distinct variety of nectarine, *Prunus persica* var. *nucipersica* cv. 'Sunectwentytwo'. The new variety was first hybridized in 2003 and selected in 2005 by Terry Bacon as breeder number: 'NE546'. The new variety was first evaluated by Terry Bacon near Wasco, Calif. in Kern County. The variety 'Sunectwentytwo' was originated by hybridization.

The new variety 'Sunectwentytwo' is characterized by early harvest and large sized fruit.

The seed parent is 'NE117' (unpatented Sun World nectarine), and the pollen parent is bulked pollen of several unpatented low chill Sun World nectarine selections. The parent varieties were first crossed in February 2003, with the date of planting of the progeny being February 2004, and the date of first flowering being February 2005. The new nectarine variety 'Sunectwentytwo' was first asexually propagated by Terry Bacon near Wasco, Kern County, Calif. in May 2005, by budding.

The new variety 'Sunectwentytwo' is distinguished from its seed parent, 'NE117', in that the new variety ripens about fourteen days earlier than 'NE117'.

The new variety 'Sunectwentytwo' has a similar ripening time as 'April Glo' (U.S. Plant Pat. No. 7,305), but is larger in size, about 70 mm versus 62 mm for 'April Glo'. The new variety 'Sunectwentytwo' is similar in appearance and shape to 'Zee Fire' (U.S. Plant Pat. No. 13,501), but harvests fourteen days earlier.

The new variety 'Sunectwentytwo' has been shown to maintain its distinguishing characteristics through successive asexual propagations by, for example, budding.

BRIEF DESCRIPTION OF THE PHOTOGRAPH

The accompanying color photographic illustration shows typical specimens of the foliage and fruit of the present new nectarine variety 'Sunectwentytwo'. The illustration shows the upper and lower surface of the leaves, an exterior and sectional view of a fruit divided across its suture plane to show flesh color, pit cavity and the stone remaining in place. The photographic illustration was taken shortly after being picked (shipping ripe) and the colors are as nearly true as is reasonably possible in a color representation of this type.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to 4 year old 'Sunectwentytwo' plants on Nemared (unpatented) rootstock, grown in the vicinity of Wasco, Kern County, Calif., during 2009, and is believed to apply to plants of the variety grown under similar conditions of soil and climate elsewhere.

TREE

General: (Measurements taken on 4 year old tree unless otherwise noted.)

*Size.*—Medium. Normal for most nectarine varieties. Reaches a height of approximately 3 meters including normal pruning.
*Spread.*—Normal for most nectarine varieties. Approximately 3 meters with normal pruning.
*Vigor.*—Moderately vigorous.
*Growth.*—Semi-upright.
*Productivity.*—Productive. Fruit set is usually two or more times desired amount for marketable size fruit. Thinning and spacing fruit is necessary.
*Form.*—Vase formed.
*Bearer.*—Regular.
*Fertility.*—Self-fertile.
*Canopy density.*—Dense.
*Hardiness.*—Hardy in all fruit growing areas of California. Winter chilling requirement is approximately 250 hours at or below 7.2 C.
*Disease resistance/susceptibility.*—No specific testing for relative plant disease resistance/susceptibility has been undertaken. Under close observation in Kern County, Calif., no particular plant/fruit disease resistance/susceptibility has been observed.

Trunk: (Measurements at approximately 30 cm above soil line.)
*Diameter.*—Approximately 16 cm, varies with soil type, fertility, climatic conditions and cultural practices.
*Texture.*—Medium shaggy, increases with age of tree.
*Trunk color.*—Outer bark is about Light Greyed-green 197D to Dark Greyed-green.
*Lenticel.*—Scare, visible where the trunk is smooth. Color: About medium Greyed-Orange 164B. Typical size.—7 mm in length and 2 mm wide.

Branches: (Measurements at approximately 90 cm above soil line.)
*Size.*—Diameter ranges from approximately 8 cm to 12 cm.
*Texture.*—Medium shaggy, increases with age.
*Color.*—About Light Greyed-green 197D to Medium Greyed-orange 166D.
*Lenticels.*—Present.
*Lenticels density.*—Approximately 2-4 per $cm^2$.
*Lenticels color.*—About Medium Greyed-orange 166D.
*Lenticels size.*—Medium.
*Lenticels length.*—Approximately 3 mm.
*Lenticels width.*—Approximately 1.5 mm.

Flowering shoots: (Data taken in July at midpoint of previous season shoots.)
*Size.*—Average diameter approximately 6 mm.
*Color.*—Topside: About Dark Greyed-orange 166B to Light Yellow-green 144C. Underside: About Light Yellow-green 144C.
*Internode length.*—Medium; approximately 10-15 cm. Midway on flowering shoot.
*Flowering shoot lenticels.*—Sparse. Color: About Light Greyed-green 196A. Diameter: Approximately 0.3 mm.
*Flowering shoot leaf buds.*—Shape: Elliptic to conical. Width: Approximately 3 mm. Length: Approximately 4 mm. Color: About Medium Greyed-green 197C.
*Flowering shoot flower buds.*—Shape: Conical. Width: Approximately 25 mm. Length: Approximately 4 mm. Color: About Medium Greyed-green 197C. Number of buds per node: Usually 2.
*Density of buds.*—Medium.
*Flower bud distribution.*—Generally isolated in groups of 2 on one year old shoots.
*Ratio of wood (leaf) buds to flowering shoots.*—1/2 on short spurs.

FOLIAGE

Leaves:
*Size.*—Medium.
*Average length.*—Medium; approximately 12-16 cm.
*Average width.*—Medium; approximately 3-4 cm.
*Thickness.*—Medium.
*Color.*—Upper surface: About Dark Yellow-green 146B. Lower surface: About Medium Yellow-green 146C.
*Form.*—Lanceolate.
*Tip.*—Cuspidate.
*Base.*—V-shaped.
*Margin.*—Crenate.
*Venation.*—Pinately veined.
*Vein color.*—About Light Yellow-green 144C to Medium Greyed-orange 176D.
*Surface texture.*—Smooth.
*Leaf blade (ratio of length to width).*—Medium; approximately 4.3/1.
*Shape in the cross section.*—Concave.
*Profile.*—Up folded.
*Leaf blade tip.*—Curved downwardly.
*Undulation of margin.*—Slight.

Petiole:
*Average length.*—Medium; approximately 14 mm.
*Average diameter.*—Approximately 2 mm.
*Color.*—About Medium Yellow-green 144A.

Stipules:
*Number/leaf bud.*—Approximately 2.
*Typical length.*—Approximately 7 mm.
*Color.*—About Dark Greyed-orange 176A when dried.
*Persistence.*—Falls off.

Leaf glands:
*Form.*—Reniform.
*Average number.*—About 2-6.
*Position.*—On both leaf base and petiole, opposite.
*Average size.*—Small; approximately 1 mm.
*Color.*—About Medium Yellow-green 144B.

FLOWERS

General:
*Flower blooming period.*—First bloom: Approximately Feb. 8, 2009. Full bloom: Approximately Feb. 15, 2009.
*Time of bloom.*—Early.
*Duration of bloom.*—Medium; approximately 13 days.
*Diameter of fully opened flower.*—Medium, approximately 32 mm.
*Flower aroma.*—Slight aroma.
*Shape.*—Rosaceous.

Peduncle:
*Length.*—Medium; approximately 4 mm.
*Diameter.*—Slender; approximately 1.5 mm.
*Color.*—About Medium Yellow-green 144A.
*Pubescence.*—Absent.

Petals:
*Number.*—5.
*Arrangement.*—Free.
*Length.*—Approximately 13 mm.
*Diameter.*—Approximately 7 mm.

*Shape.*—Elliptic.
*Apex shape.*—Rounded.
*Base shape.*—Narrows, Cuneate.
*Color.*—About Red-purple 62B.
*Surface texture.*—Smooth.
*Margins.*—Slightly undulating.
*Claw length.*—Short.
*Margin waviness.*—Weak.
*Base angle.*—Medium.
*Division of upper margin.*—Entire.
*Pubescence of inner surface.*—Absent.
*Pubescence of outer surface.*—Absent.

Sepals:
*Number.*—5.
*Length.*—Approximately 7 mm.
*Diameter.*—Approximately 4 mm.
*Shape.*—Elliptic.
*Color.*—About Medium Red-purple 64B outside surface.
*Surface texture.*—Smooth.
*Margins.*—Entire.
*Positioning.*—Not touching petals or receptacle when opened.
*Pubescence of inner surface.*—Absent.
*Pubescence of outer surface.*—Absent.

Stamens:
*Number.*—Many, approximately 45-55.
*Average length.*—Approximately 12 mm.
*Filament color.*—About Light Red-purple 62C, darkening to about Medium Red-purple 64B as flower ages.
*Anther color.*—About Medium Red-purple 61B.
*Flower pollen color.*—About Dark Yellow-orange 22A when dried.
*Position.*—Perigynous.

Pistil:
*Number.*—Usually one.
*Average length.*—Approximately 18 mm.
*Ovary diameter.*—Approximately 1.5 mm.
*Pubescence.*—None.
*Stigma extension in comparison to anthers.*—Usually above.
*Frequency of supplementary pistils.*—Few.

Receptacle:
*Depth.*—Medium.
*Pubescence of inner surface.*—Absent.
*Pubescence of outer surface.*—Absent.

FRUIT

General: (Description taken near Wasco, Kern County, Calif.)
*Harvest.*—Date of first pick: Approximately May 1, 2009. Date of last pick: Approximately May 10, 2009.
Maturity when described: Firm-mature.
Season ripening: Very early.
Position of maximum diameter: Towards the middle.
Symmetry about the suture: Somewhat symmetric.
Size:
*Length* (*stem end to apex*).—Approximately 70 mm.
*Diameter in line with suture plane.*—Approximately 70 mm.
*Diameter perpendicular to suture plane.*—Approximately 65 mm.
*Average weight.*—Approximately 145 gm.
Form:
*Viewed from apex.*—Rounded, nearly symmetrical
*Viewed from side, facing suture.*—Rounded, nearly symmetrical. .
*Viewed from side, perpendicular to suture.*—Rounded, nearly symmetrical.
Apex shape: Rounded.
Fruit stem cavity:
*Shape.*—Rounded.
*Depth.*—Medium; approximately 0.8 cm.
*Breadth.*—Approximately 1.5 cm.
*Width.*—Medium.
Fruit stem:
*Length.*—Approximately 10 mm.
*Diameter.*—Approximately 2.5 mm.
*Color.*—About Medium Greyed-orange 164B.
*Adherence to stone.*—Medium.
Fruit skin:
*Thickness.*—Medium.
*Adherence to flesh.*—Strong.
*Surface texture.*—Medium.
*Pubescence.*—None.
*Bloom.*—Slight.
*Ground color.*—About Dark Yellow-orange 17D when mature.
*Overcolor.*—About Medium Red 47B covering 95% of the fruit skin.
*Taste.*—Neutral.
*Reticulation.*—Absent.
*Roughness.*—Absent.
*Tenacity.*—Tenacious to flesh.
*Tendency to crack.*—Slight, in wet season.
Flesh:
*Ripens.*—Evenly.
*Texture.*—Firm, melting.
*Fibers.*—Few.
*Flavor.*—Mild.
*Brix.*—Approximately 12°.
*Juice.*—Moderate.
*Aroma.*—Slight.
*Color.*—About Medium Yellow-orange 15C when mature.
*Acidity.*—Medium.
*Eating quality.*—Good.
*Stone/flesh ratio.*—About 1/4.
*Firmness.*—Firm.
Pit cavity size:
*Length* (*diameter in line with suture plane*).—Approximately 30-35 mm.
*Diameter perpendicular to suture plane.*—Approximately 20 mm.
*Color.*—About Medium Yellow-orange 15C.
Fruit use: Fresh market.
Fruit shipping and keeping quality: Good, holds well in cold storage and maintains good firmness and eating quality, minimal bruising and scarring in packing and shipping trials.
Stone: (Measurements taken on dried stones.)
*Stone freeness.*—Clings over entire surface.
*Degree of adherence to flesh.*—Medium.
*Stone size.*—Size compared to Fruit: Medium. Length (Diameter in line with suture plane): Approximately 30-35 mm. Diameter perpendicular to suture plane: Approximately 20 mm. Width of Stalk End: Medium; approximately 3 mm. Angle of Stalk end: Right angle. Hilum: Oval.

*Stone form.*—Viewed from side: Oval. Viewed from ventral side: Flattened. Viewed from stem end: Oval, nearly symmetric.

*Stone shape.*—Base shape: Nearly straight. Apex shape: Pointed.

*Stone surface.*—Pitted throughout.

*Stone halves.*—Nearly symmetric.

*Stone ridges.*—Rounded continuous.

*Stone outgrowing keel.*—Partially developed.

*Stone tendency to split.*—Slight in wet season.

*Stone color.*—About Medium Greyed-orange 166C.

*Position of maximum.*—Toward middle.

*Ventrical edge.*—Medium.

*Dorsal edge.*—Narrow grooves, interrupted.

What is claimed is:

1. A new and distinct nectarine tree as herein described and illustrated.

* * * * *

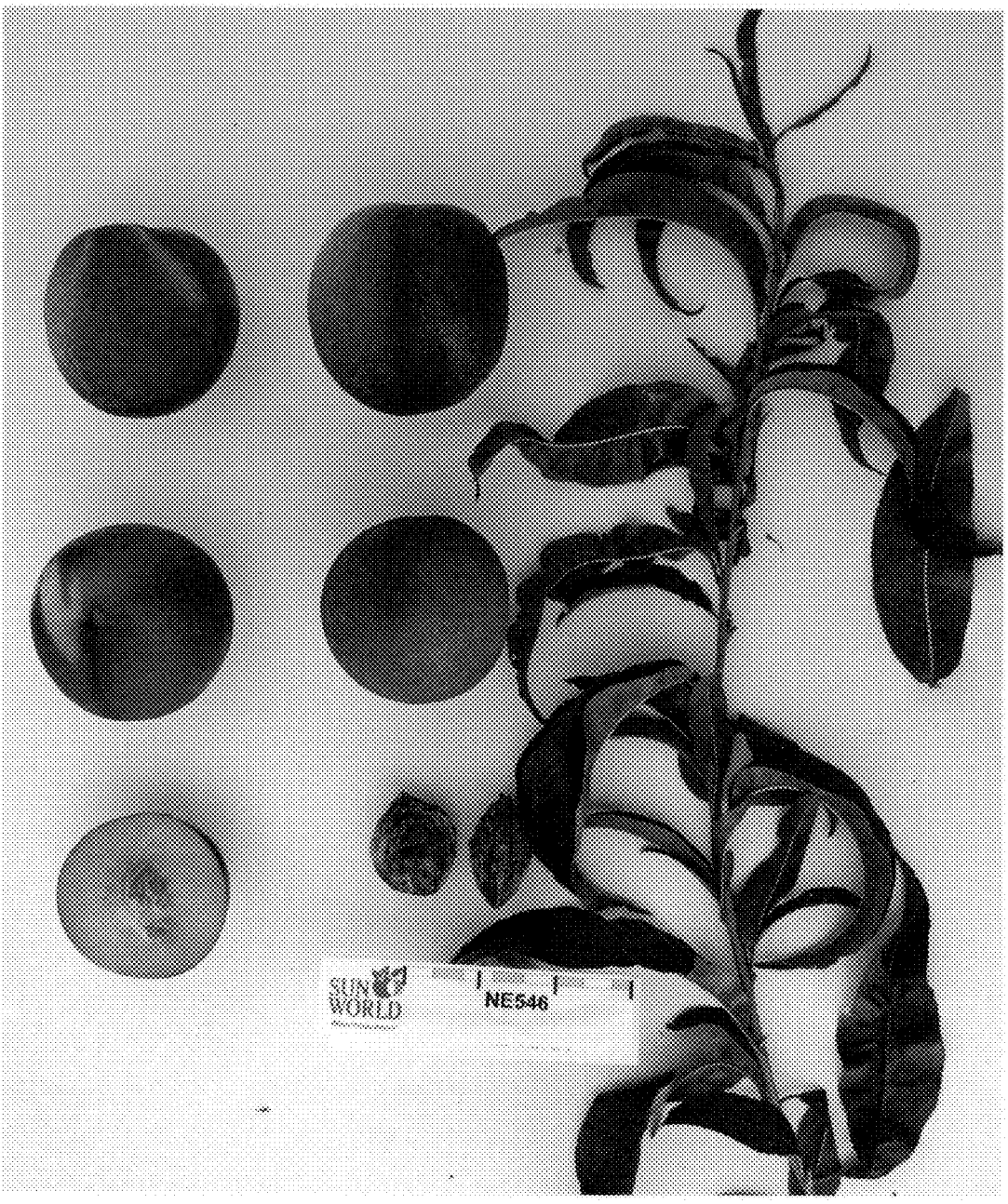
SUN WORLD
NE546

UNITED STATES PATENT AND TRADEMARK OFFICE

CERTIFICATE OF CORRECTION

PATENT NO. : PP22,448 P3
APPLICATION NO. : 12/657348
DATED : January 10, 2012
INVENTOR(S) : Terry A. Bacon It is certified that error appears in the above-identified patent and that said Letters Patent is hereby corrected as shown below:

Title page, item (50), line 1, after "Latin name: *Prunus persica* var.", remove "nucipersia" and insert therefore --nucipersica--.

On page 3, Column 1, line 30, after "Dark-Greyed-green", insert --197A; inner bark is about Dark Greyed-orange 177A to Medium Greyed-orange 174B.--.

On page 3, Column 4, line 19, remove "Pinately" and insert therefore --Pinnately--.

On page 5, Column 5, line 65-66, remove "symmetrical. ." and insert therefore --symmetrical.--.

Signed and Sealed this
Nineteenth Day of June, 2012

David J. Kappos

David J. Kappos
*Director of the United States Patent and Trademark Office*